United States Patent [19]

Thomas

[11] Patent Number: 4,887,459
[45] Date of Patent: Dec. 19, 1989

[54] TURF GAUGE FOR MEASURING THE HARDNESS OF A GOLD GREEN

[75] Inventor: Frank Thomas, Chester, N.J.

[73] Assignee: U.S. Golf Association, Far Hills, N.J.

[21] Appl. No.: 215,547

[22] Filed: Jul. 6, 1988

[51] Int. Cl.⁴ ............................................. G01N 3/42
[52] U.S. Cl. .......................................... 73/81; 73/84
[58] Field of Search ................................... 73/81, 84

[56] References Cited

U.S. PATENT DOCUMENTS

| | | | |
|---|---|---|---|
| 1,637,421 | 8/1927 | Lipschutz | 73/81 |
| 2,117,985 | 5/1938 | Ridenour | 73/84 |
| 2,130,751 | 9/1938 | van der Meer | 73/84 |
| 2,421,449 | 6/1947 | Zuber | 73/81 |
| 3,214,966 | 11/1965 | Menzies | 73/79 |
| 3,498,120 | 3/1970 | MacMillan | 73/81 X |
| 3,782,365 | 1/1974 | Pinna | 73/81 X |
| 4,061,021 | 12/1977 | Baldwin et al. | 73/84 |
| 4,116,047 | 9/1978 | Hejkal | 73/81 |
| 4,136,554 | 1/1979 | Larson | 73/81 |
| 4,302,967 | 12/1981 | Dufey | 73/84 |

FOREIGN PATENT DOCUMENTS 1330507  8/1987  U.S.S.R. .......................... 73/84 UX

*Primary Examiner*—Tom Noland
*Attorney, Agent, or Firm*—Kenyon & Kenyon

[57] ABSTRACT

The turf gauge includes a housing, a probe assembly which is spring biased within the housing with a probe to penetrate into a green and a scale member to indicate the depth of penetration of the probe. A handle of the turf gauge acts to lock the scale member in place so that a reading can be obtained after withdrawal of the gauge from the green. The construction of the turf gauge permits ready replacement of spacer rings for changing the pre-stress of the spring on the probe assembly.

12 Claims, 2 Drawing Sheets

U.S. Patent   Dec. 19, 1989   Sheet 1 of 2   4,887,459
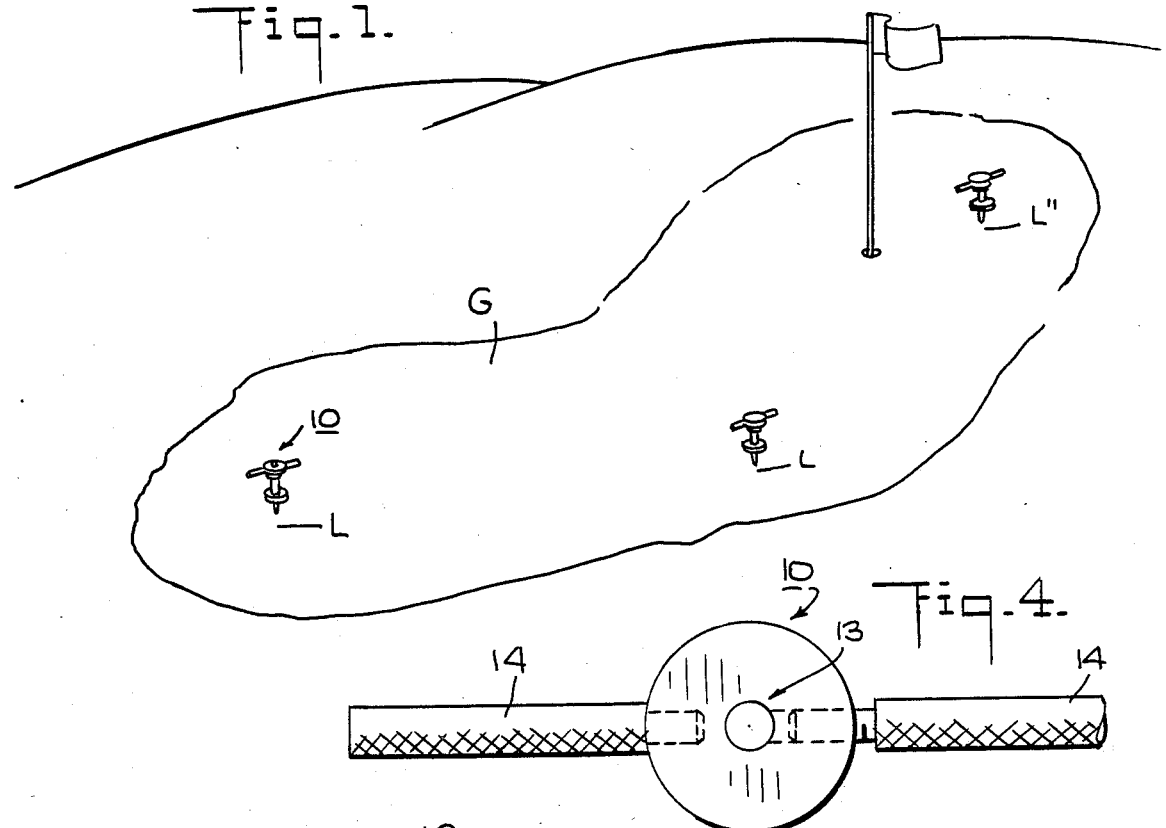
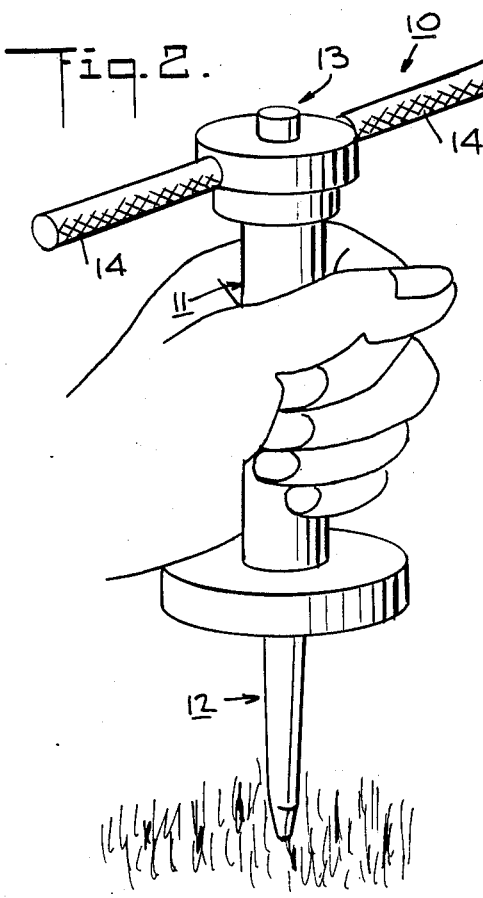
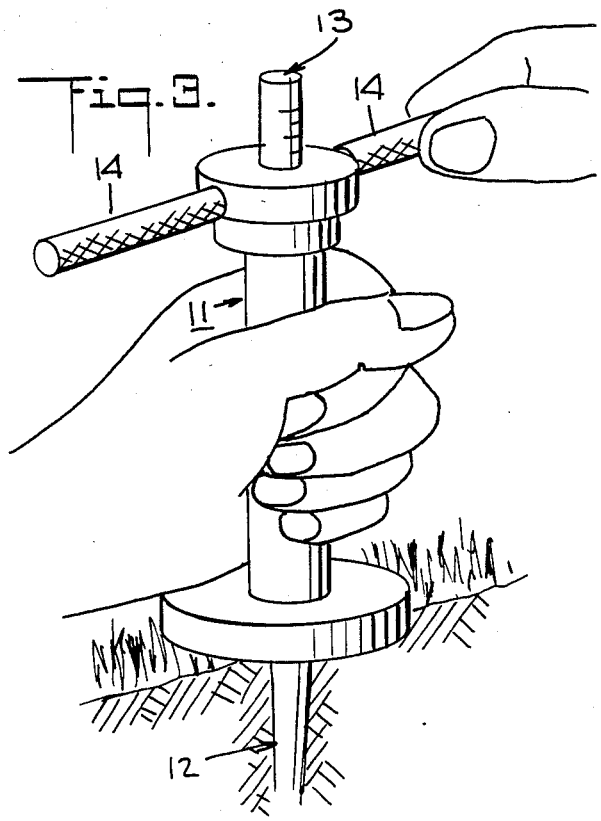

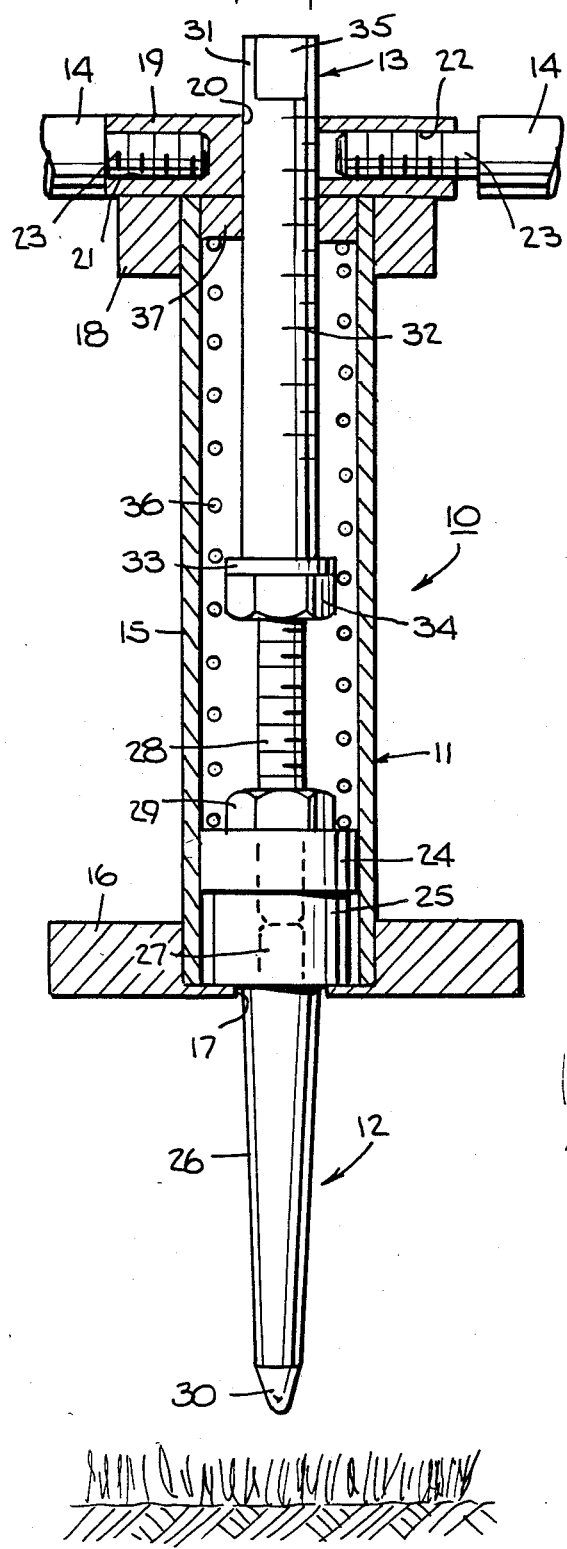
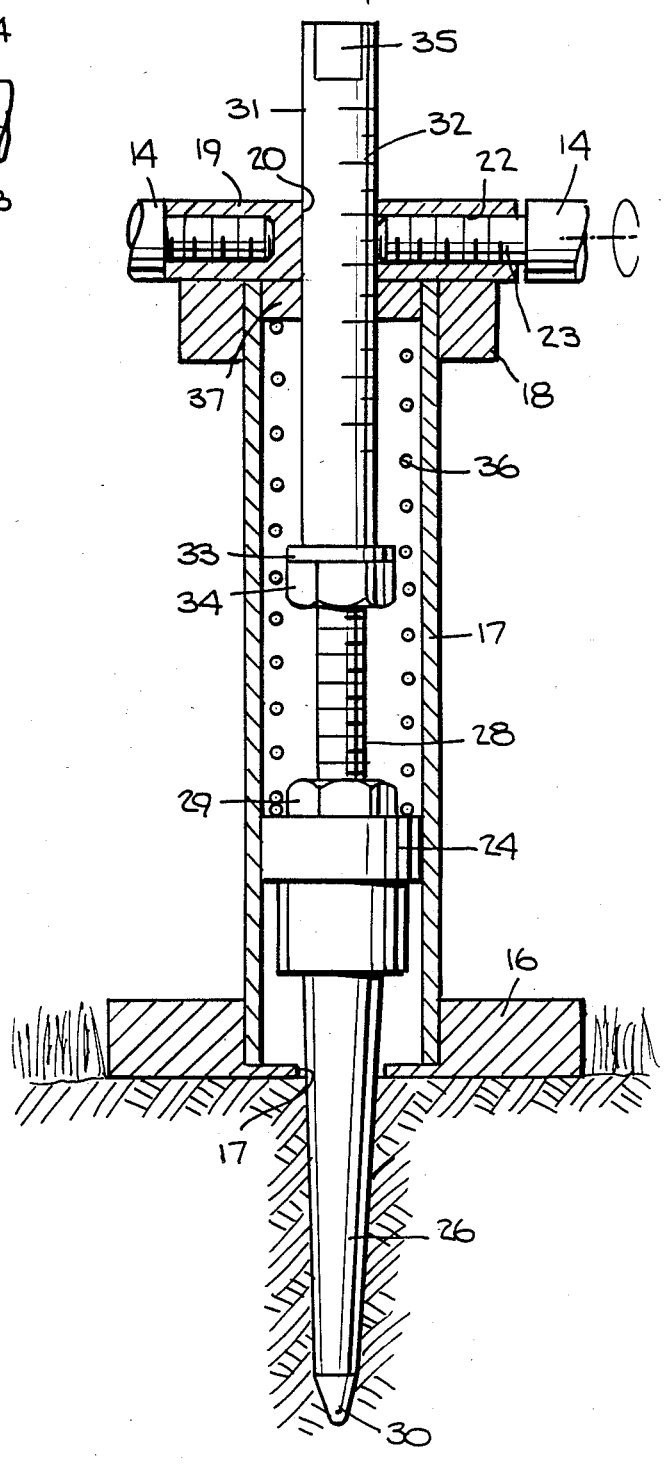

TURF GAUGE FOR MEASURING THE HARDNESS OF A GOLD GREEN

BACKGROUND OF THE INVENTION

1. Field of the Invention

This invention relates to a turf gauge. More particularly, this invention relates to a turf gauge for measuring the hardness of golf greens. As is known, golf courses are generally maintained so that fairways, roughs and greens meet certain standards. However, difficulties frequently arise in attempting maintain the eighteen green of any given golf course, particularly the hardness of a green, so that each has similar surface characteristics. Depending upon the degree of watering, wind conditions, exposure to the elements and the like, hardness may easily vary. The maintenance of such greens is particularly acute for tournament play conditions. For example, a great degree of care is usually taken that the greens have the same hardness so that a ball impacting on any one green will perform in the same manner for all greens.

2. Description of Prior Related Art

In the past, various types of penetrometers and hardness measuring device have been known. For example, U.S. Pat. Ser. No. 4,061,021 describes a recording penetrometer which provides a depth-penetration resistance graph as the penetrometer is forced into the ground. To this end, the penetrometer includes a probe for penetrating the ground as well as a second probe which terminates in a ground engaging foot portion at one end while the upper end cooperates with a scriber apparatus for scribing on pressure sensitive paper mounted on a drum.

U.S. Pat. Ser. No. 3,214,966 describes an instrument for indicating the "going", that is, the degree of hardness of race courses and the like. This instrument, however, relies upon a weight which is dropped onto a spring and a scale calibrated to measure the rebound of the weight as a measure of the "going". Reference is also made to penetrometers having a protection which is caused to penetrate a ground surface in response to a predetermined application of force with the depth of penetration being used to give an indication of the hardness of the ground or "going".

U.S. Pat. Ser. No. 2,130,751 describes an apparatus for determining the resistance of the ground and is similar to that described in U.S. Pat. Ser. No. 3,214,966.

U.S. Pat. Ser. No. 2,117,985 describes a soil plasticity testing apparatus for measuring resistance to penetration by water. In this case, the apparatus includes a needle which is penetrated into the earth at a selected rate of speed with the resistance encountered measured by a spring responsive ring.

U.S. Pat. Ser. No. 2,421,449 describes a hardness measuring instrument for materials such as soft rubber. In this case, a pin is mounted by two springs in a floating manner to abut against a plunger which is movable with the pin and which is held in place by a spring biased plunger in order to give a measure of the movement of the pin.

U.S. Pat. Ser. No. 3,498,120 describes a fabric strength measuring device which includes a handle in which a blade is placed against a fabric to be tested and is forced into a handle against a spring until the end of the blade is even with the end of the handle. The force requirement for that amount of displacement is then a measure of the hardness of the material.

U.S. Pat. Ser. No. 1,637,421 describes a pressure indicator which records the amount of pressure necessary to cause a person being treated to experience sensitiveness to any pain produced by reasons of the pressure.

In general, all of the devices described in the above-noted patents are rather cumbersome to use.

SUMMARY OF THE INVENTION

Accordingly, it is an object of the invention to provide a relatively simple device for measuring the hardness of a golf green.

It is another object of the invention to be able to maintain a golf green at a uniform hardness.

It is another object of the invention to provide a simple turf gauge from which hardness measurements can be easily obtained.

Briefly, the invention provides a turf gauge for measuring the hardness of a golf green which includes a housing having a flat base at one end with a bore extending therethrough, a probe assembly movably mounted within the housing with a probe extending through the housing bore for movement between an extended position and a retracted position and a spring within the housing biasing the probe into the extended position under a predetermined force.

In addition, the turf gauge includes a member which is adjustably secured to the probe assembly and which extends out of the housing at an end opposite the probe. This member includes a scale with indicia to cooperate with an upper end of the housing to indicate the extent of projection of the probe from the housing into the green.

Still further, the turf gauge includes a locking member on the housing for locking the scale member relative to the housing in order to fix the probe and obtain a measurement of the depth of penetration of the probe into the green. This locking member may constitute a rotatable handle which extends perpendicularly from the housing and which has a threaded end threadably received in the housing for selectively abutting and clamping the scale member relative to the housing.

When in use, the turf gauge is manually pressed against the surface of a green so that the probe may penetrate into the green under the biasing force of the spring. Depending upon the hardness or softness of the green, the probe will penetrate into the green more or less. That is, the softer the green, the more the penetration. Since the spring exerts a constant force, the depth of penetration will be a measure of the hardness of the green.

After the probe has penetrated, the rotatable handle can be turned so as to lock the scale member in place. Upon removal from the green, the scale can be read to determine the amount of penetration that took place. This measurement may then be correlated with other measurements taken over the green so as to determine the hardness throughout the green. Appropriate maintenance can then be applied so as to subsequently obtain a uniform hardness across the surface of the green.

The housing is constructed of relatively simple parts so that the spring loading can be changed from time-to-time to accommodate measurements for relatively softer or harder surfaces. To this end, the housing includes a cylinder in which the spring is mounted, a flat base plate at one end of the cylinder defining the flat base of the gauge and central bore for passage of the probe assembly, a ring press-fitted onto the cylinder at an opposite end and a top plate removably secured to the ring with a central bore for passage of the scale member. In addition, one or more spacer rings may be provided between the spring and the top plate for pre-stressing the spring.

In order to calibrate this device or to change the spacer ring from time-to-time, the top plate is secured by screws or bolts to the press-fitted ring so that the top plate can be removed to expose the interior of the cylinder. The spacer ring can then be removed or replaced by a thicker or thinner ring and the top plate then secured in place.

BRIEF DESCRIPTION OF THE DRAWING FIGURES

These and other objects and advantages of the invention will become more apparent from the following detailed description taken in conjunction with the accompanying drawings wherein:

FIG. 1 illustrates a perspective view of a golf green with a turf gauge according to the invention at a location to determine the hardness thereat;

FIG. 2 illustrates a perspective view of the turf gauge immediately prior to penetrating into a golf green;

FIG. 3 illustrates a view similar to FIG. 2 with the turf gauge probe penetrated into the green;

FIG. 4 illustrates a top view of the upper end of the turf gauge in accordance with the invention;

FIG. 5 illustrates a cross sectional view of the turf gauge prior to penetration into a golf green; and FIG. 6 illustrates a cross sectional view similar to FIG. 5 with the probe penetrating into a golf green.

DETAILED DESCRIPTION

Referring to FIG. 1, the turf gauge 10 is used to determine the hardness of a golf green G at various locations L, L', L". While a multiplicity of locations may be measured, only three are indicated in FIG. 1.

As indicated in FIG. 2, the turf gauge 10 is sized so as to be manually handled and is of compact construction.

Referring to FIGS. 2 and 5, the turf gauge 10 includes a housing 11, a probe assembly 12, a scale member 13 and a pair of handles 14.

Referring to FIG. 5, the housing 11 is of four piece construction and includes a cylinder 15, for example of metal, a flat base plate 16 mounted at one end of the cylinder 15 with a central bore 17 therein, a ring 18 which is press-fitted onto the cylinder 15 at an opposite end and a top plate 19 which is removably secured to the ring 18, for example by threaded screws or bolts (not shown) and which has a central bore 20 therein.

The flat base plate 16 is recessed to receive the cylinder 15 in press-fit relation. Alternatively, the flat base plate 16 may be secured to the cylinder 15 in any other suitable manner.

The top plate 19 is provided with a pair of threaded bores 21, 22 to receive threaded stems 23 of the handles 14. In addition, one bore 22 extends through the top plate 19 so that the threaded stem 23 of one handle 14 may be abutted against the scale member 13 in order to secure the member 13 relative to the top plate 19 for purposes as explained below.

The probe assembly 12 is movably mounted within the cylinder 15 and includes a cap 24 having a threaded bore 25, a tapered probe 26 which has a threaded stem 27 at the upper end, as viewed, which is threaded into the bore 25 of the cap 24, and a threaded stem 27 which is threaded into the bore 25 of the cap 24 and extends upwardly therefrom. A jam nut 29 is also threaded on the stem 28 against the cap 24 to secure the stem 28 to the cap 24 while the stem 28 fixes the probe 26 in place.

The probe 26 is provided with a tip 30 having a different angle of taper from the remainder of the probe 26. This tip 30 may also be a separate piece which can be mounted in the probe proper, for example, for replacement purposes.

The scale member 13 includes a cylindrical rod 31 which is threaded onto the stem 28 and which has a scale 32 of indicia thereon for cooperating with the top plate 19 to indicate the extent of extension of the probe 26 beyond the base plate 16. A stop washer 33 and a jam nut 34 are also provided about the stem 28 to secure the rod 31 in place. The rod 31 is also provided with a pair of flats 35 at the upper exposed end in order to facilitate adjustment of the rod 31 on the stem 28. As indicated, the rod 31 is slidably mounted within the bore 20 of the top plate 19.

As indicated in FIG. 2, each handle 14 is provided with a knurled surface and extends radially from the housing 11.

Referring to FIG. 5, a spring 36 is also positioned between the cap 24 and the cap plate 19 in order to bias the probe 26 outwardly of the cylinder 15 under a predetermined force. In addition, a spacer ring 37 is provided between the spring 36 and the top plate 19 to permit adjustment of the spring force.

In use, the turf gauge 10 is grasped manually by the handles 14 and positioned over a golf green G at a location as indicated in FIG. 1. The probe 26 is then forced into the green until the base plate 16 abuts against the green G, as indicated in FIG. 3. Depending upon the hardness or softness of the green, the probe 26 will penetrate more or less. Specifically, the softer the green, the more the penetration. The depth of penetration is indicated by the extent to which the rod 31 of the scale member 13 projects upwardly from the top plate 19 of the housing 11. After the base plate 16 abuts the green G, the rotatable handle 14 is rotated as indicated in FIGS. 3 and 5 so as to lock the rod 31 relative to the top plate 19. The turf gauge 10 may then removed from the green G. At this time, the rod 31 remains in place so that a reading can be obtained as to the depth of penetration of the probe 26. The obtained reading can then be correlated with other readings taken about the green G in order to determine the hardness of the green at the various locations.

Once a determination of the hardness of a green has been obtained, a maintenance schedule can be prepared in order to make the green of uniform hardness throughout. The other greens of a golf course can be correlated in similar manner so that all of the greens have a predetermined hardness and, preferably a similar hardness.

In the event that a need arises to change the force on the spring 36, the top plate 19 can be removed by unthreading of the screws which hold the top plate 19 to the ring 18. After removal, the spacer ring 37 can be removed and the top plate 19 replaced so that the pre-stress on the spring 36 is reduced or a thicker ring can be put in place so as to increase the pre-stress on the spring 36.

The invention thus provides a turf gauge of relatively simple construction which can be readily manipulated by hand to obtain a hardness reading of a golf green so as to develop a standard for the purpose of common reference.

Further, the invention provides a turf gauge of relatively simple construction wherein a spring force can be changed from time-to-time in a simple manner.

Still further, the invention provides a turf gauge of sturdy construction which can provide reliable readings over extended periods of time and which can be correlated with the performance of a ball when impacting the green. Based on quantitative measurements of green hardness, a prescribed hardness can be obtained for greens for tournament play conditions.

What is claimed is:

1. A turf gauge for measuring the hardness of a golf green comprising
   a housing having a flat base at one end with a bore extending therethrough;
   a probe assembly movably mounted within said housing for movement between an extended position and a retracted position, said assembly including a probe extending through said bore in said base in said extended position for penetrating into the golf green;
   a spring within said housing biasing said probe assembly into said extended position under a predetermined force;
   a member adjustably secured to said probe assembly and extending out of said housing at an end opposite said probe, said member having a scale thereon with indicia to cooperate with an upper end of said housing to indicate the extent of projection of said probe from said housing into the green; and
   a locking member on said housing for locking said member relative to said housing to fix said probe relative to said housing to obtain a measurement of the depth of penetration of said probe into the green.

2. A turf gauge as set forth in claim 1 wherein said probe assembly includes a cap slidably mounted in said housing and having a threaded bore receiving one end of said probe therein in threaded relation and a threaded stem threaded into said bore and threadably receiving said member thereon.

3. A turf gauge as set forth in claim 2 wherein said locking member includes a rotatable handle extending perpendicularly of said housing and having a threaded end threadably received in said housing for selectively abutting and clamping said member relative to said housing.

4. A turf gauge as set forth in claim 1 wherein said locking member includes a rotatable handle extending perpendicularly of said housing and having a threaded end threadably received in said housing for selectively abutting and clamping said member relative to said housing.

5. A turf gauge as set forth in claim 1 wherein said housing includes a cylindrical sleeve and a base plate mounted at one end of said sleeve with said flat base thereon.

6. A turf gauge as set forth in claim 1 wherein said probe is tapered.

7. A turf gauge as set forth in claim 1 which further comprises a pair of handles secured to said housing and extending radially thereof.

8. A turf gauge comprising
   a housing including a cylinder, a flat base plate mounted at one end of said cylinder with a central bore therein, a ring press-fitted onto said cylinder at an opposite end and a top plate removably secured to said ring with a central bore therein;
   a probe assembly movably mounted within said cylinder, said assembly including a probe extending through said bore of said base plate;
   a spring in said cylinder between said top plate and said base plate biasing said probe assembly in a direction out of said cylinder under a predetermined force; and
   a member secured to said probe assembly for movement therewith relative to said cylinder, said member having a scale thereon for cooperating with said top plate to indicate the extent of projection of said probe from said flat base plate.

9. A turf gauge as set forth in claim 8 which further comprises a removable spacer ring between said spring and said top plate for pre-stressing said spring.

10. A turf gauge as set forth in claim 8 which further comprises a pair of handles extending radially from said top plate.

11. A turf gauge as set forth in claim 10 wherein at least one of said handles is rotatable and has an end threadably received in said top plate for selectively abutting and clamping said member relative to said top plate.

12. A turf gauge as set forth in claim 8 wherein said base plate is recessed to receive said cylinder in press-fit relation.

* * * * *

UNITED STATES PATENT AND TRADEMARK OFFICE
CERTIFICATE OF CORRECTION

PATENT NO. : 4,887,459

DATED : Dec. 19, 1989

INVENTOR(S) : FRANK THOMAS

It is certified that error appears in the above-identified patent and that said Letters Patent is hereby corrected as shown below:

```
Front page, [54] "GOLD" Should be -GOLF-
Column 1, line 3 "GOLD" Should be -GOLF-
Column 1, lines 27, 36, 48, 50, 51, 57 and 64, "Pat. Ser. No."
      Should be -Pat. No.-
Column 2, line 3 "Pat. Ser. No." Should be -Pat. No.-
```

Signed and Sealed this

Fifteenth Day of January, 1991

*Attest:*

HARRY F. MANBECK, JR.

*Attesting Officer*   *Commissioner of Patents and Trademarks*